United States Patent
Torii et al.

(10) Patent No.: US 12,193,705 B2
(45) Date of Patent: Jan. 14, 2025

(54) PIPE FOR FLUID SUPPLY AND AIR FEEDING SYSTEM INCLUDING PIPE FOR FLUID SUPPLY

(71) Applicant: OLYMPUS CORPORATION, Tokyo (JP)

(72) Inventors: Shinya Torii, Tokyo (JP); Kunitoshi Hiraga, Tama (JP); Koji Yamaoka, Hamura (JP); Takefumi Uesugi, Tachikawa (JP); Yuma Kasuya, Hachioji (JP); Keita Kimura, Hachioji (JP); Nanaho Togi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1203 days.

(21) Appl. No.: 16/944,333

(22) Filed: Jul. 31, 2020

(65) Prior Publication Data
US 2020/0360049 A1    Nov. 19, 2020

Related U.S. Application Data

(63) Continuation of application No. PCT/JP2018/037926, filed on Oct. 11, 2018.

(30) Foreign Application Priority Data

Feb. 1, 2018    (JP) .................................. 2018-016480

(51) Int. Cl.
*A61B 17/34*    (2006.01)
*A61B 17/00*    (2006.01)
*A61B 90/00*    (2016.01)

(52) U.S. Cl.
CPC .... *A61B 17/3423* (2013.01); *A61B 17/00234* (2013.01); *A61B 17/3474* (2013.01);
(Continued)

(58) Field of Classification Search
CPC .......... A61B 17/3423; A61B 17/00234; A61B 17/3474; A61B 90/06; A61B 2090/064;
(Continued)

(56) References Cited

U.S. PATENT DOCUMENTS 4,180,068 A * 12/1979 Jacobsen ............. A61M 5/1582
                                                                    604/44
2005/0004512 A1   1/2005 Campbell et al.
(Continued)

FOREIGN PATENT DOCUMENTS

JP    2005-245772 A    9/2005
JP    2007-185387 A    7/2007
(Continued)

OTHER PUBLICATIONS

International Search Report dated Dec. 18, 2018 received in PCT/JP2018/037926.

*Primary Examiner* — Nathan R Price
*Assistant Examiner* — John A Doubrava
(74) *Attorney, Agent, or Firm* — Scully, Scott, Murphy & Presser, P.C.

(57) ABSTRACT

A pipe for fluid supply includes: a pipe configured integrally with an air feeding conduit and a pressure measurement conduit; inlets of the air feeding conduit and the pressure measurement conduit; outlets of the air feeding conduit and the pressure measurement conduit; and tube connection portions provided at the respective inlets in the pipe such that an angle between a vertical direction of the respective inlets and a vertical direction of each the respective outlets is 30° to 60°.

20 Claims, 17 Drawing Sheets

(52) U.S. Cl.
CPC ........ *A61B 90/06* (2016.02); *A61B 2090/064* (2016.02); *A61B 2217/007* (2013.01)

(58) Field of Classification Search
CPC ..... A61B 2217/007; A61B 2017/3419; A61M 13/003; A61M 2039/1077; A61M 2205/3344
See application file for complete search history.

(56) References Cited

U.S. PATENT DOCUMENTS

| | | | | |
|---|---|---|---|---|
| 2007/0088275 | A1* | 4/2007 | Stearns | A61B 17/3462 604/164.01 |
| 2012/0029479 | A1* | 2/2012 | Kraushaar | A61M 39/105 604/533 |
| 2015/0151071 | A1* | 6/2015 | Von Moger | A61M 16/0875 128/202.27 |
| 2018/0310958 | A1* | 11/2018 | Silver | A61B 17/3421 |

FOREIGN PATENT DOCUMENTS

| | | |
|---|---|---|
| JP | 2010-502360 A | 1/2010 |
| WO | 2008/030256 A1 | 3/2008 |

\* cited by examiner

M1<M3

M2<M4

M3 > M1

M4 > M2

PIPE FOR FLUID SUPPLY AND AIR FEEDING SYSTEM INCLUDING PIPE FOR FLUID SUPPLY

CROSS REFERENCE TO RELATED APPLICATION

This application is a continuation application of PCT/JP2018/037926 filed on Oct. 11, 2018 and claims benefit of Japanese Application No. 2018-016480 filed in Japan on Feb. 1, 2018, the entire contents of which are incorporated herein by this reference.

BACKGROUND OF THE INVENTION

1. Field of the Invention

The present invention relates to a pipe for fluid supply including a pipe attached to a body wall of a subject and configured integrally with an air feeding conduit configured to feed air into the subject and a pressure measurement conduit configured to measure a pressure in the subject in real time, and to an air feeding system including the pipe for fluid supply.

2. Description of the Related Art

A procedure is well known in which air, for example, carbon dioxide air, is supplied to a subject, for example, a body cavity, using an air feeding system to perform observation, treatment or the like on the inside of the body cavity in a state where the body cavity is expanded.

The air feeding system is well known to include a fluid supply device, for example, an insufflation device, and a tube in which one end is attached to the body wall of the subject to be inserted into the body cavity and the other end is connected to the insufflation device.

In the observation, treatment or the like using such an air feeding system, a method is used in which a step of feeding air into the body cavity through the tube from the insufflation device and a step of measuring a pressure through the tube in a state where the air feeding is stopped are repeated intermittently until the inside of the body cavity reaches a set pressure suitable for treatment.

Such an air feeding method is effective because the inside of the body cavity can be quickly expanded to a set pressure when the inside of the body cavity is a large space.

However, for example, when the known TATME (transanal total mesorectal excision) procedure is used for a small space such as a rectum that is treated through an anus, the small space is expanded quickly even when the amount of air to be fed is small.

Therefore, it is necessary to reduce the amount of air to be fed per unit time period and continuously feed the air up to the set pressure in order to prevent vibration in the body cavity associated with the air feeding. For this reason, it is necessary to continuously measure the pressure in the body cavity and adjust the amount of air to be fed.

Therefore, a configuration of an air feeding system is well known, in which two tubes of an air feeding tube and a pressure measurement tube connected to an insufflation device are attached to the body wall and inserted into the body cavity, thereby capable of continuously measuring the pressure in the body cavity using the pressure measurement tube and continuously feeding air up to the set pressure in the body cavity using the air feeding tube.

In Japanese Patent Application Laid-Open Publication No. 2010-502360, an air feeding system is disclosed in which an air feeding tube and a pressure measurement tube are connected to a pipe, in which an air feeding conduit and a pressure measurement conduit are integrally provided (separately provided inside), so as to communicate with the air feeding conduit and the pressure measurement conduit, respectively, and the pipe is inserted into the body cavity.

According to such a configuration of the air feeding system, when the pipe attached to the body wall and inserted into the body cavity is unexpectedly detached from the body wall, not only the pressure measurement conduit but also the air feeding conduit is detached from the body wall, to thereby be capable of preventing excessive air feeding into the body cavity.

In addition, since the pressure does not rise no matter how much air is fed, an operator can easily recognize that the pipe is detached from the body wall.

However, in the air feeding system disclosed in Japanese Patent Application Laid-Open Publication No. 2010-502360, the air feeding tube and the pressure measurement tube are connected to tube connection portions provided at respective inlets, respectively, such that the angle formed by a vertical direction of each of outlets which is a second opening of the air feeding conduit and the pressure measurement conduit provided in the pipe with respect to a vertical direction of each of inlets which is a first opening is about 90°.

In addition, the pipe is attached to the body wall in different manners depending on the operator, but a case is considered where the operator attaches the pipe such that the air feeding tube and the pressure measurement tube are hung on a floor or where the operator attaches the pipe so as to be located on the a body surface of a lying examinee, for example, on the abdomen.

SUMMARY OF THE INVENTION

A pipe for fluid supply according to an aspect of the present invention includes: a pipe attached to a body wall of a subject and configured integrally with an air feeding conduit configured to feed air into the subject and a pressure measurement conduit configured to measure a pressure in the subject in real time; first openings provided respectively at one end of the air feeding conduit provided in the pipe and at one end of the pressure measurement conduit provided in the pipe; second openings provided respectively at another end of the air feeding conduit provided in the pipe and at another end of the pressure measurement conduit provided in the pipe; and tube connection portions provided respectively in the respective first openings in the pipe, and connected to the air feeding conduit and the pressure measurement conduit at the respective first openings such that an angle between a vertical direction of each of the first openings and a vertical direction of each of the second openings is 30° to 60°.

An air feeding system including a pipe for fluid supply according to another aspect of the present invention includes: the pipe for fluid supply; an air feeding tube having one end connected to the tube connection portion of the air feeding conduit; a pressure measurement tube having one end connected to the tube connection portion of the pressure measurement conduit; and a fluid supply device connected to another end of the air feeding tube and another end of the pressure measurement tube and configured to feed air into a subject through the air feeding tube and the air feeding conduit and to measure a pressure in the subject through the pressure measurement conduit and the pressure measurement tube.

DETAILED DESCRIPTION OF THE PREFERRED EMBODIMENT

An embodiment of the present invention will be described below with reference to the drawings. Note that the drawings are schematic, relations between thicknesses and widths of respective members and ratios of the thicknesses of the respective members are different in relations and ratios from the actual members. Naturally, dimensional relations and ratios may be different from each other between the drawings.

Figure 1:
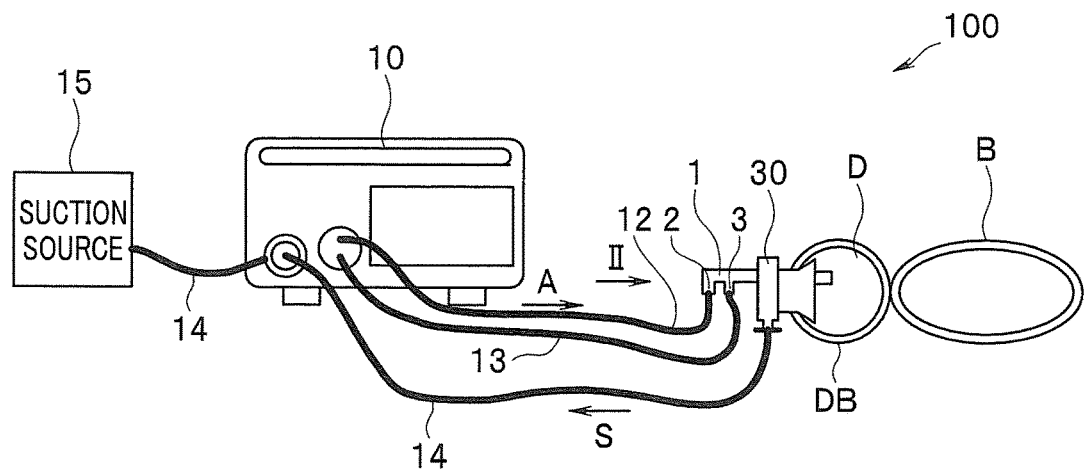
FIG. 1 is a diagram showing a configuration of an air feeding system including a pipe for fluid supply of the present embodiment.
Figure 2:
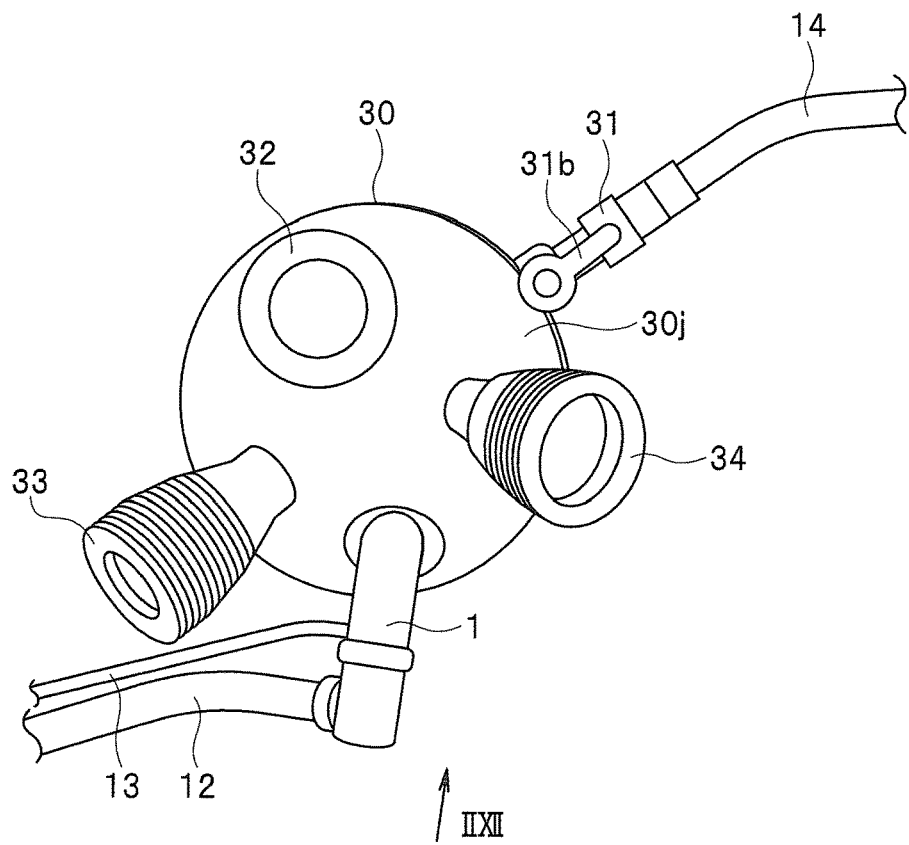
FIG. 2 is a plan view showing a state where the pipe for fluid supply shown in FIG. 1 is stuck in a fixing device when viewed in a II direction in FIG. 1.

FIG. 1 is a diagram showing a configuration of an air feeding system including a pipe for fluid supply of the present embodiment, and FIG. 2 is a plan view showing a state where the pipe for fluid supply shown in FIG. 1 is stuck in a fixing device when viewed in a II direction in FIG. 1.

Figure 3:
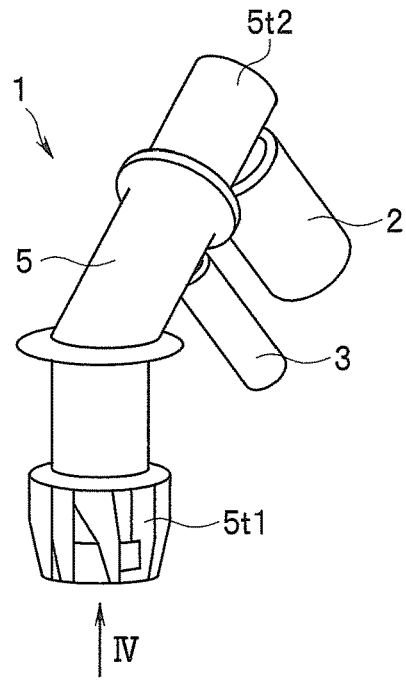
FIG. 3 is a perspective view of the pipe for fluid supply shown in FIG. 1.
Figure 4:
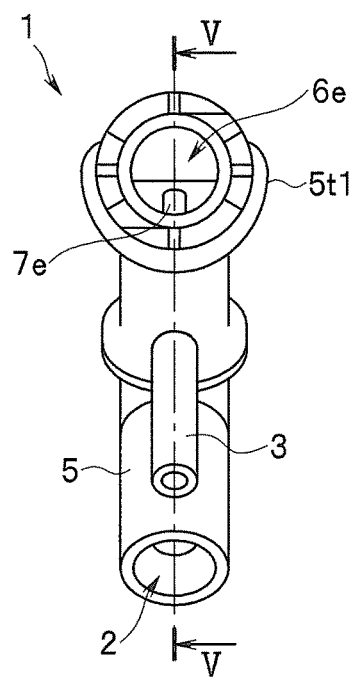
FIG. 4 is a plan view of the pipe for fluid supply shown in FIG. 3 when viewed in a IV direction in FIG. 3.
Figure 5:
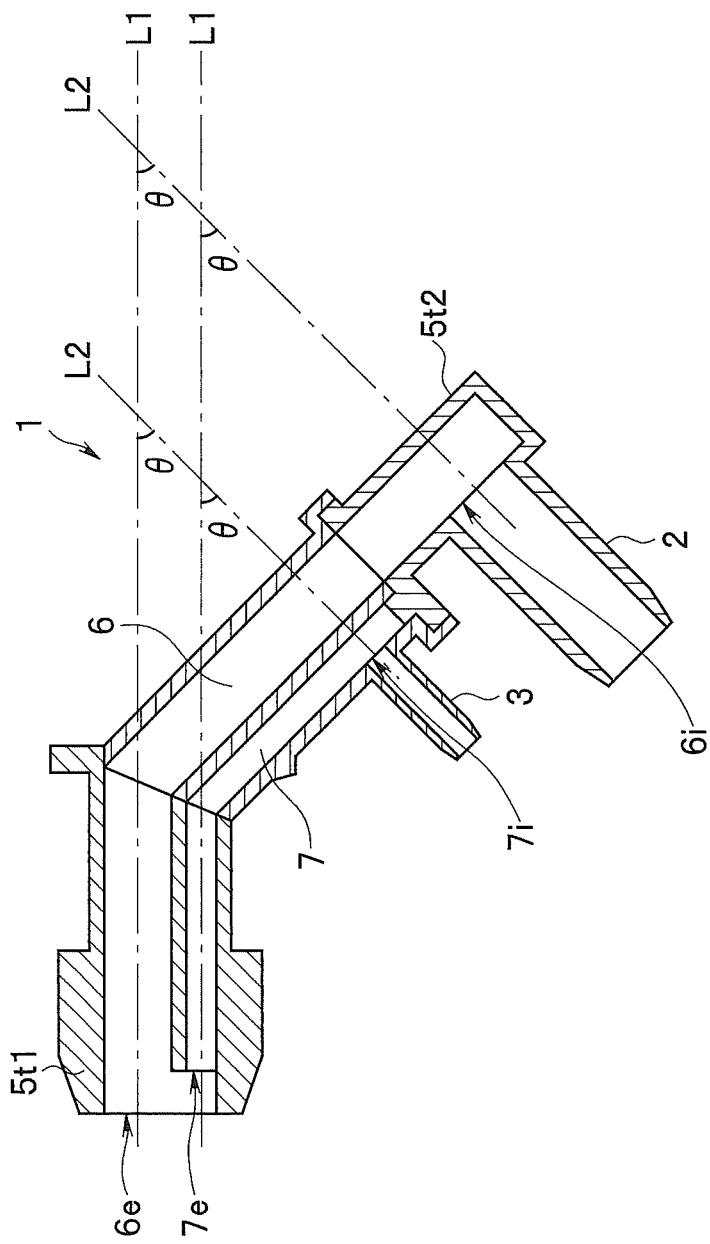
FIG. 5 is a cross-sectional view of the pipe for fluid supply taken along a line V-V in FIG. 4.

Further, FIG. 3 is a perspective view of the pipe for fluid supply shown in FIG. 1, FIG. 4 is a plan view of the pipe for fluid supply shown in FIG. 3 when viewed in a IV direction in FIG. 3, and FIG. 5 is a cross-sectional view of the pipe for fluid supply taken along a line V-V in FIG. 4.

As shown in FIG. 1, an air feeding system 100 includes, as main components, a pipe for fluid supply 1, an insufflation device 10 that is a fluid supply device, an air feeding tube 12, a pressure measurement tube 13, a suction tube 14, a suction source 15, and a fixing device (perforated device) 30 that is an insertion target.

The pipe for fluid supply 1 includes a pipe (also referred to as pipe shell) 5 as shown in FIGS. 3 to 5. As shown in FIG. 5, the pipe 5 includes inside thereof an air feeding conduit 6 through which air A is fed into a subject, for example, rectum D, and a pressure measurement conduit 7 configured to measure a pressure in the rectum D in real time and has a smaller diameter than the air feeding conduit 6, the air feeding conduit 6 and the pressure measurement conduit 7 being configured integrally with the pipe 5.

Note that the term "configured integrally" as used herein means that the respective conduits 6 and 7 are formed integrally with the pipe 5 such that the air feeding conduit 6 and the pressure measurement conduit 7 are disposed independently and separately in the pipe 5.

The pipe 5 is assumed to be a disposable type, and is replaced with a new one every time the pipe 5 is used.

At an end portion (hereinafter, referred to as a proximal end portion) 5*t*2 in an extending direction of the pipe 5, respective inlets 6*i* and 7*i* serving as first openings provided respectively at one end of the air feeding conduit 6 and one end of the pressure measurement conduit 7 are formed so as to be exposed on an outer surface of the pipe 5.

At an end portion (hereinafter, referred to as a distal end portion) 5*t*1 on the side opposite to the position where the respective inlets 6*i* and 7*i* in the extending direction of the pipe 5 are formed, respective outlets 6*e* and 7*e* serving as second openings provided respectively at the other end of the air feeding conduit 6 and the other end of the pressure measurement conduit 7 are formed so as to be exposed on the outer surface of the pipe 5.

Tube connection portions 2 and 3 are provided at the respective inlets 6*i* and 7*i*, respectively, to be connected to the air feeding conduit 6 and the pressure measurement conduit 7.

As shown in FIG. 1, one end of the air feeding tube 12 is connected, for example, adhesively fixed, to the tube connection portion 2, and one end of the pressure measurement tube 13 is connected, for example, adhesively fixed, to the tube connection portion 3.

As shown in FIG. 1, the other end of the air feeding tube 12 and the other end of the pressure measurement tube 13 are connected to the insufflation device 10.

The insufflation device 10 feeds the air A into the rectum D of an examinee B via the air feeding tube 12 and the air feeding conduit 6, and measures an internal pressure of the subject in real time via the pressure measurement conduit 7 and the pressure measurement tube 13.

As shown in FIG. 5, the tube connection portions 2 and 3 are provided at the respective inlets 6*i* and 7*i* such that angles θ between a vertical direction L2 of the respective inlets 6*i* and 7*i* and a vertical direction L1 of the respective outlets 6*e* and 7*e* are 30° to 60°, and preferably 45°.

In other words, as shown in FIGS. 3 to 5, the pipe 5 is bent at a midway position, at which the distal end portion 5*t*1 and the proximal end portion 5*t*2 are coupled to each other, in the extending direction.

Further, as shown in FIG. 5, the outlet 7*e* is opened at a recessed position at which a lower step is formed on the side of the inlets 6*i* and 7*i*, that is, on the side of the proximal end portion 5*t*2 relative to the outlet 6*e*. Therefore, the outlet 7*e* is opened in the air feeding conduit 6.

End faces of the respective outlets 6*e* and 7*e* are opened at the distal end portion 5*t*1 of the pipe 5 in a direction perpendicular to the vertical direction L1, and the outlet 6*e* is opened to an end face of the distal end portion 5*t*1.

As shown in FIG. 1, the gel-like fixing device 30 has a frame fixed to an entrance of an intestinal wall DB, which is a body wall of the rectum D, that is, an anus, and has a configuration in which the distal end portion 5*t*1 side of the pipe 5 in the pipe for fluid supply 1 penetrates a gel portion 30*j*.

As shown in FIG. 2, the fixing device 30 is configured such that respective inlet ports 32 to 34, to which an endoscope, a treatment instrument and the like in addition to the pipe for fluid supply 1 can be inserted, can penetrate the gel portion 30*j* similarly to the pipe for fluid supply 1.

The fixing device 30 includes a suction connector 31 connected to the other end of the suction tube 14, one end of which is connected to the suction source 15, and the suction connector 31 has a configuration in which an internal conduit is opened and closed by a valve body 31*b*.

Accordingly, when the conduit of the suction connector 31 is opened by the valve body 31*b* and the suction source 15 is driven, air in the rectum D, for example, a smoke generated by the treatment, is sucked through the suction tube 14, and thus a good visual field in the rectum D can be secured.

The fixing device 30 may include an air feeding connector including a valve body. The shape of the fixing device 30 shown in FIG. 2 is merely an example, and it goes without saying that the shape is not limited to such a shape.

Figure 6:
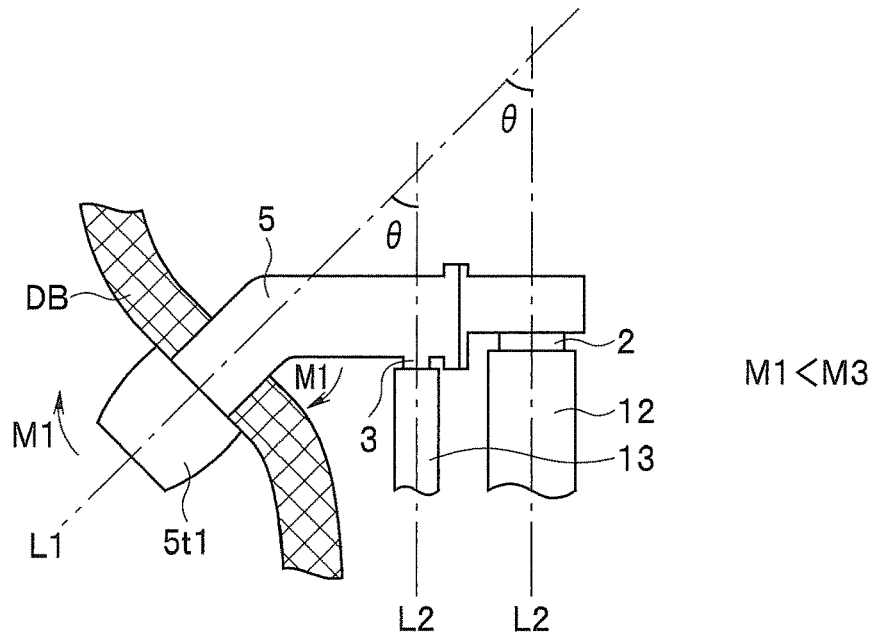
FIG. 6 is a diagram schematically showing a state where the pipe for fluid supply is inserted into a rectum in a state where an air feeding tube and a pressure measurement tube are attached to respective tube connection portions of the pipe in the pipe for fluid supply shown in FIG. 3 so as to hang on a floor.
Figure 7:
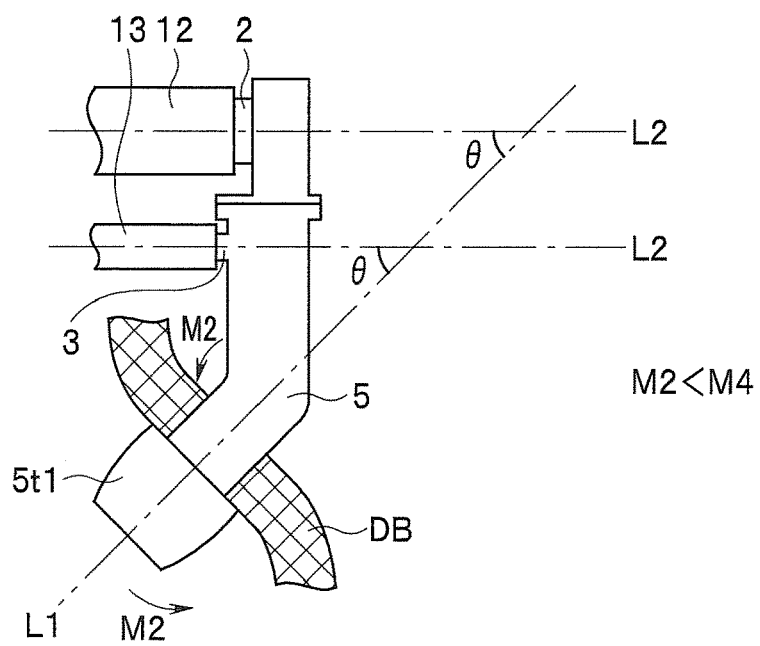
FIG. 7 is a diagram schematically showing a state where the pipe for fluid supply is inserted into a rectum in a state where the air feeding tube and the pressure measurement tube are attached to the respective tube connection portions of the pipe in the pipe for fluid supply shown in FIG. 3 so as to be located on an abdomen of a lying examinee.

Operations of the present embodiment will be described below with reference to FIGS. 6 to 9. FIG. 6 is a diagram schematically showing a state where the pipe for fluid supply is inserted into the rectum in a state where the air feeding tube and the pressure measurement tube are attached to the respective tube connection portions of the pipe in the pipe for fluid supply shown in FIG. 3 so as to hang on a floor, and FIG. 7 is a diagram schematically showing a state where the pipe for fluid supply is inserted into the rectum in a state where the air feeding tube and the pressure measurement tube are attached to the respective tube connection portions of the pipe in the pipe for fluid supply shown in FIG. 3 so as to be located on an abdomen of a lying examinee.

Figure 8:
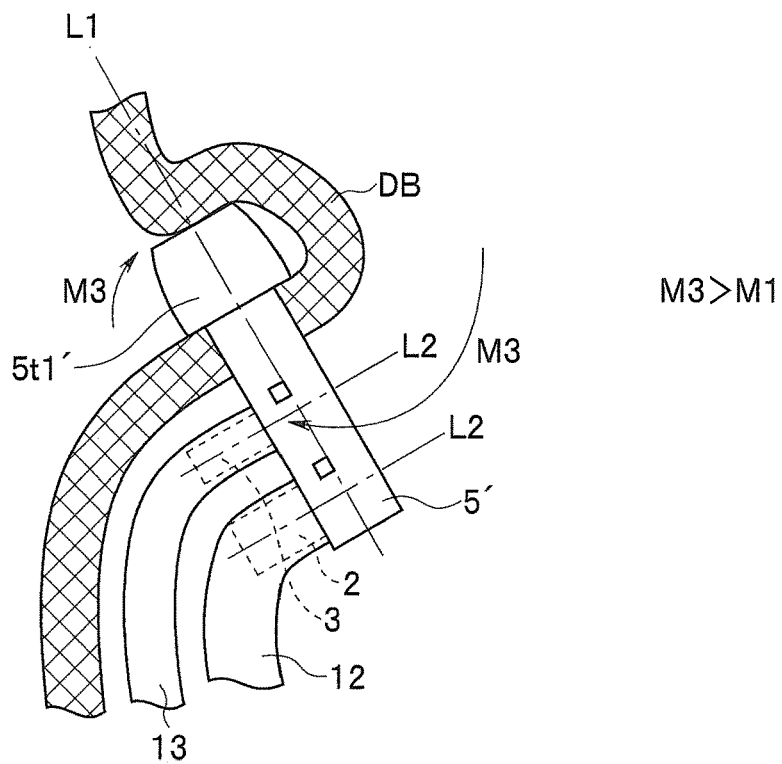
FIG. 8 is a diagram schematically showing a state where a pipe for fluid supply is inserted into a rectum in a state where the air feeding tube and the pressure measurement tube are attached to respective tube connection portions of a pipe in a pipe for fluid supply according to the related art so as to hang on a floor.
Figure 9:
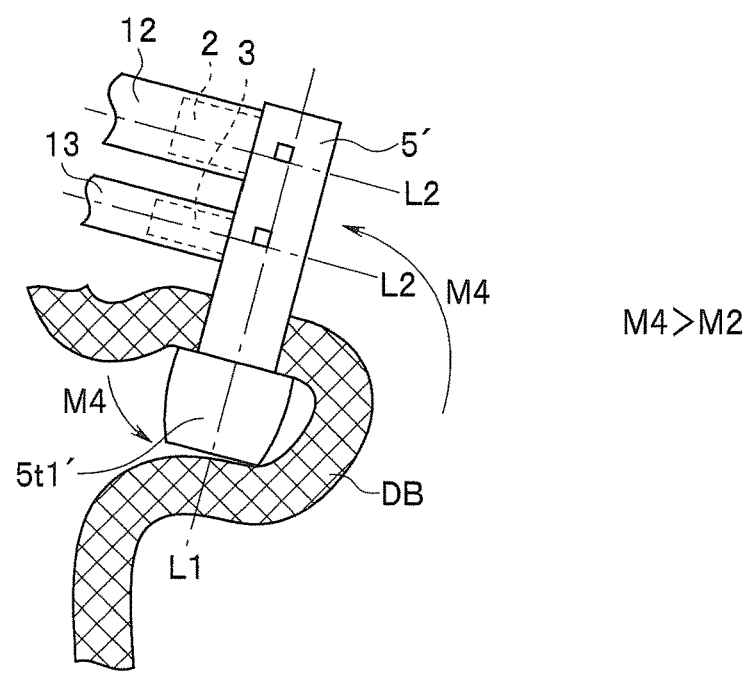
FIG. 9 is a diagram schematically showing a state where the pipe for fluid supply is inserted into a rectum in a state where the air feeding tube and the pressure measurement tube are attached to the respective tube connection portions of the pipe in the pipe for fluid supply according to the related art so as to be located on an abdomen of a lying examinee.

FIG. 8 is a diagram schematically showing a state where a pipe for fluid supply is inserted into the rectum in a state where the air feeding tube and the pressure measurement tube are attached to respective tube connection portions of a pipe in a pipe for fluid supply according to the related art so as to hang on a floor, and FIG. 9 is a diagram schematically showing a state where the pipe for fluid supply is inserted into the rectum in a state where the air feeding tube and the pressure measurement tube are attached to the respective tube connection portions of the pipe in the pipe for fluid supply according to the related art so as to be located on the abdomen of a lying examinee.

In FIGS. 6 to 9, the fixing device 30 is not shown to simplify the drawings. In other words, a case is shown as an example in which the distal end portion 5*t*1 of the pipe 5 is directly inserted into the rectum D.

In the state where the distal end portion 5*t*1 of the pipe 5 in the pipe for fluid supply 1 is inserted into the rectum D and in the state where the tubes 12 and 13 are attached to the respective tube connection portions 2 and 3 so as to hang on the floor as shown in FIGS. 6 and 8, due to weight of the tubes 12 and 13, a force acts on the proximal end portion 5*t*2 side of the pipe 5 to rotate the pipe 5 toward the floor provided downward in the direction of gravity via the tubes 12 and 13.

Therefore, the pipe 5 or 5' located outside the rectum D rotates by M1 or M3, and a force also acts on the distal end portion 5*t*1 or 5*t*1' to rotate the distal end portion 5*t*1 or 5*t*1' by M1 or M3 upward in the direction of gravity.

At this time, the tube connection portions 2 and 3 are respectively provided at the inlets 6*i* and 7*i* in the pipe 5 of the pipe for fluid supply 1 of the present embodiment such that the angle θ between the vertical direction L2 of each of the inlets 6*i* and 7*i* and the vertical direction L1 of each of the outlets 6*e* and 7*e* is 30° to 60°, and preferably 45°. For this reason, a rotation range of the pipe 5 is smaller than a rotation range of the pipe 5' according to the related art in which the tube connection portions 2 and 3 are respectively provided at the inlets 6*i* and 7*i* such that the angle θ between the vertical direction L2 of each of the inlets 6*i* and 7*i* and the vertical direction L1 of each of the outlets 6*e* and 7*e* is 90° as shown in FIG. 8, that is, a relation of M1<M3 is satisfied.

Therefore, each of the outlets 6*e* and 7*e* is buried in the intestinal wall DB due to the rotation range M3 in the pipe 5' according to the related art shown in FIG. 8, but each of the outlets 6e and 7e is less likely to be buried in the intestinal wall DB due to the rotation range M1 in the pipe 5 of the present embodiment.

In the state where the distal end portion 5t1 of the pipe 5 in the pipe for fluid supply 1 is inserted into the rectum D and in the state where the tubes 12 and 13 are attached to the respective tube connection portions 2 and 3 so as to be located on the abdomen of the examinee B lying on their back as shown in FIGS. 7 and 9, the tubes 12 and 13 are pulled with respect to the pipe 5, and thus a force acts on the proximal end portion 5t2 side of the pipe 5 to rotate the pipe 5 upward in the direction of gravity via the tubes 12 and 13.

Therefore, the pipe 5 or 5' located outside the rectum D rotates by M2 or M4, and a force also acts on the distal end portion 5t1 or 5t1' to rotate the distal end portion 5t1 or 5t1' by M2 or M4 downward in the direction of gravity.

At this time, a rotation range of the pipe 5 in the pipe for fluid supply 1 according to the present embodiment is smaller than a rotation range of the pipe 5' according to the related art for the same reason as above, that is, a relation of M2<M4 is satisfied. Therefore, each of the outlets 6e and 7e is buried in the intestinal wall DB due to the rotation range M4 in the pipe 5' according to the related art shown in FIG. 9, but each of the outlets 6e and 7e is less likely to be buried in the intestinal wall DB due to the rotation range M2 in the pipe 5 of the present embodiment.

From the above, the pressure in the rectum D can be continuously measured via the outlet 7e regardless of the movement of the pipe 5 or the direction in which the tubes 12 and 13 crawl.

The above is also applied to a case where the distal end portion 5t1 of the pipe 5 is inserted into the rectum D via the fixing device 30, and the respective outlets 6e and 7e are less likely to be buried in the gel portion 30j of the fixing device 30. Other operations are similar to operations of the related art.

In the pipe 5 of the pipe for fluid supply 1 according to the present embodiment, as described above, it is indicated that the tube connection portions 2 and 3 are provided at the inlets 6i and 7i, respectively, such that the angle θ between the vertical direction L2 of each of the inlets 6i and 7i and the vertical direction L1 of each of the outlets 6e and 7e is 30° to 60°, and preferably 45°.

Thereby, as shown in FIGS. 6 and 7, even when the pipe 5 rotates by M1 or M3 through the respective tubes 12 and 13, the rotation range M1 or M3 is smaller than the rotation range M2 or M4 of the pipe 5' according to the related art, so that the respective outlets 6e and 7e are less likely to be buried in the intestinal wall DB or the gel portion 30j.

Accordingly, since at least the outlet 7e can be prevented from being blocked regardless of the direction in which the tubes 12 and 13 crawl along with the attachment direction of the pipe 5 or the rotation of the pipe 5 after the attachment, the pressure in the rectum D can be continuously measured in real time with accuracy.

From the above description, it is possible to provide the pipe for fluid supply 1 having the configuration capable of preventing at least the outlet 7e of the pressure measurement conduit 7 provided in the pipe 5 from being buried by the attachment direction and movement of the pipe 5, and the air feeding system 100 including the pipe for fluid supply 1.

Figure 10:
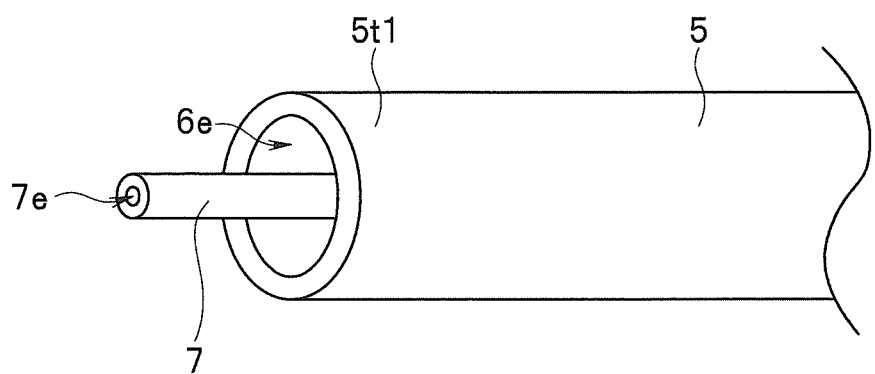
FIG. 10 is a partial perspective view schematically showing a modification in which an outlet of the pressure measurement conduit in the pipe of the pipe for fluid supply shown in FIG. 3 protrudes further forward than an outlet of the air feeding conduit.

A modification will be described below with reference to FIG. 10. FIG. 10 is a partial perspective view schematically showing a modification in which the outlet of the pressure measurement conduit in the pipe of the pipe for fluid supply shown in FIG. 3 protrudes further forward than the outlet of the air feeding conduit.

In the above-described present embodiment, it is indicated that the outlet 7e of the pressure measurement conduit 7 is recessed toward the proximal end portion 5t2 side relative to the outlet 6e of the air feeding conduit 6 so as to have a level difference (step) with respect to the outlet 6e.

On the contrary, as shown in FIG. 10, the outlet 7e may be located so as to protrude further than the outlet 6e.

Thereby, even when the outlet 6e moves out of the rectum D due to the movement of the pipe 5, the outlet 7e is more likely to be located in the rectum D, so that it is possible to continuously measure the pressure in the rectum D.

Figure 11:
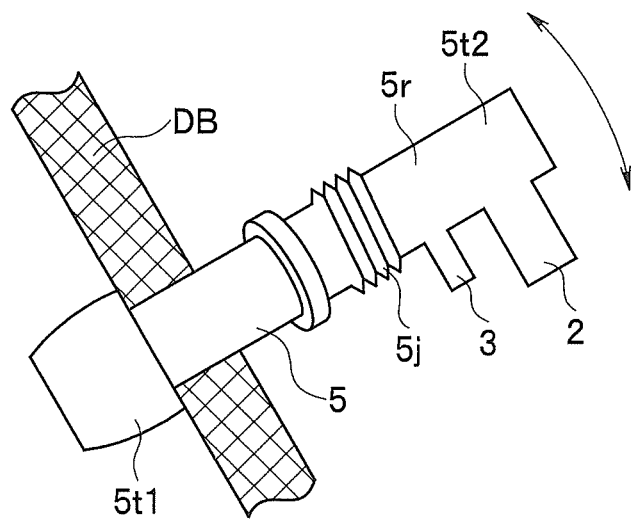
FIG. 11 is a perspective view showing a modification in which a bellows portion is provided at a midway position in an extending direction of the pipe in the pipe for fluid supply shown in FIG. 3.

Another modification will be described below with reference to FIG. 11. FIG. 11 is a perspective view showing a modification in which a bellows portion is provided at a midway position in the extending direction of the pipe in the pipe for fluid supply shown in FIG. 3.

In the pipe 5 of the pipe for fluid supply 1 according to the present embodiment described above, it is indicated that the tube connection portions 2 and 3 are provided at the inlets 6i and 7i, respectively, such that the angle θ between the vertical direction L2 of each of the inlets 6i and 7i and the vertical direction L1 of each of the outlets 6e and 7e is 30° to 60°, and preferably 45°.

The configuration is not limited to the above configuration. As shown in FIG. 11, a bellows portion 5j is provided at the midway position in the extending direction of the pipe 5, and an angle of a portion 5r on the proximal end portion 5t2 side with respect to the distal end portion 5t1 in the pipe 5 is arbitrarily variable with the bellows portion 5j, so that an effect similar to the effect of the present embodiment described above can be obtained even when, due to the variable angle, the tube connection portions 2 and 3 are provided at the inlets 6i and 7i, respectively, such that the angle θ between the vertical direction L2 of each of the inlets 6i and 7i and the vertical direction L1 of each of the outlets 6e and 7e is 30° to 60°, and preferably 45°.

Figure 12:
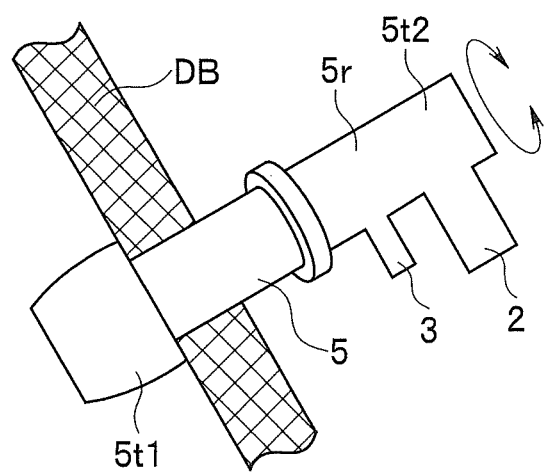
FIG. 12 is a perspective view showing a modification in which a portion on a proximal end portion side of the pipe in the pipe for fluid supply shown in FIG. 3 is configured to be rotatable.

Another modification will be described below with reference to FIG. 12. FIG. 12 is a perspective view showing a modification in which a portion on the proximal end portion side of the pipe in the pipe for fluid supply shown in FIG. 3 is configured to be rotatable.

As shown in FIG. 12, a portion 5r on the proximal end portion 5t2 side in the extending direction of the pipe 5 may be rotatable relative to the distal end portion 5t1 side.

According to such a configuration, even in the case where the tube connection portions 2 and 3 are not provided at the inlets 6i and 7i, respectively, in the manner such that the angle θ between the vertical direction L2 of each of the inlets 6i and 7i and the vertical direction L1 of each of the outlets 6e and 7e is 30° to 60°, and preferably 45° as in the above-described present embodiment, that is, even in the case where the angle θ is 90° as in the related art, the portion 5r rotates even if an external force is applied to each of the tubes 12 and 13, to thereby release the external force. As a result, the distal end portion 5t1 side of the pipe 5 hardly moves in the rectum D.

Therefore, an effect similar to the effect of the above-described present embodiment can be obtained.

Figure 13:
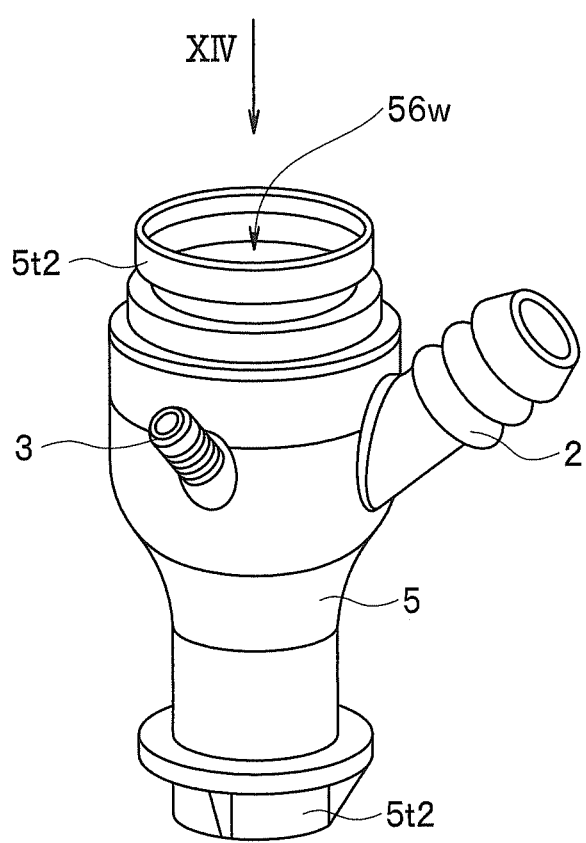
FIG. 13 is a perspective view showing a modification of the pipe for fluid supply shown in FIG. 3.
Figure 14:
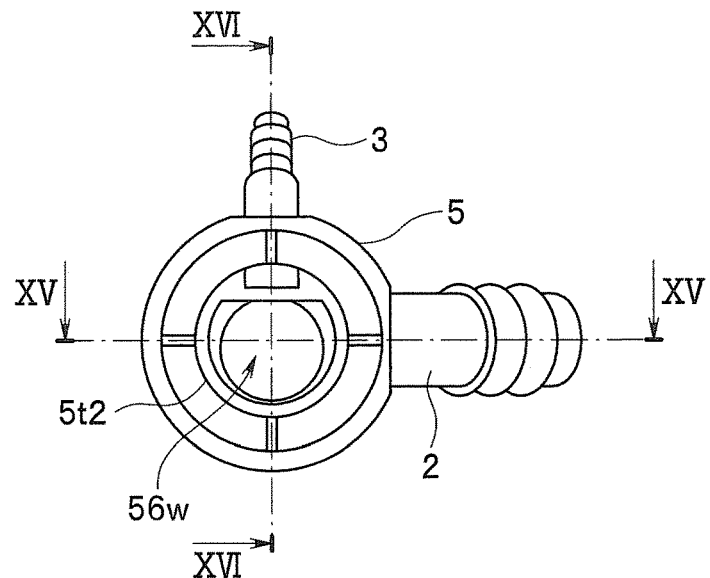
FIG. 14 is a top view of the pipe for fluid supply shown in FIG. 13 when viewed in a XIV direction in FIG. 13.
Figure 15:
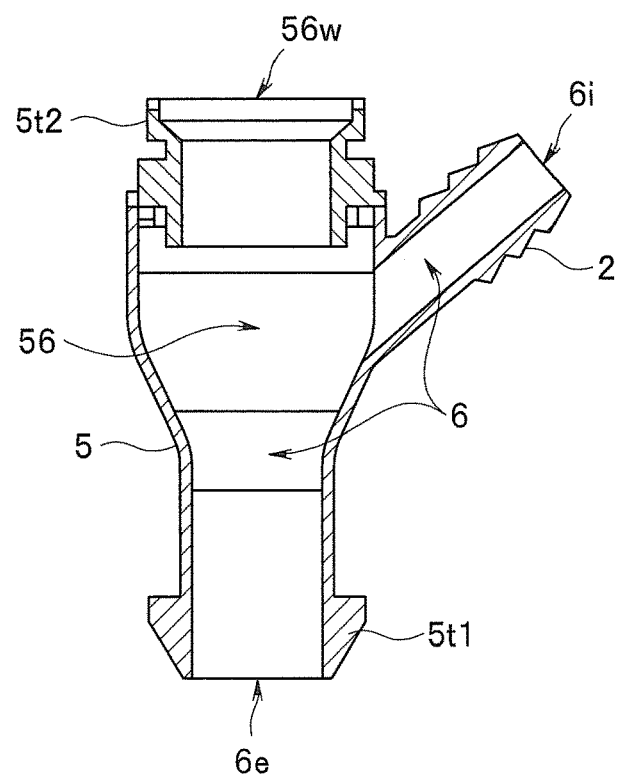
FIG. 15 is a cross-sectional view of the pipe for fluid supply taken along a line XV-XV in FIG. 14.
Figure 16:
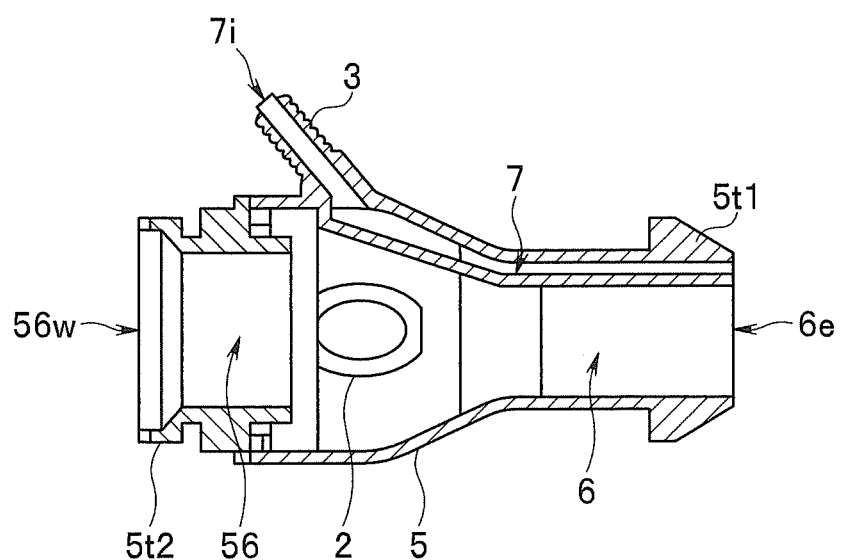
FIG. 16 is a cross-section view of the pipe for fluid supply taken along a line XVI-XVI in FIG. 14.

Another modification will be described below with reference to FIGS. 13 to 16. FIG. 13 is a perspective view showing a modification of the pipe for fluid supply shown in FIG. 3, FIG. 14 is a top view of the pipe for fluid supply shown in FIG. 13 when viewed in a XIV direction in FIG. 13, FIG. 15 is a cross-sectional view of the pipe for fluid supply taken along a line XV-XV in FIG. 14, and FIG. 16 is a cross-section view of the pipe for fluid supply taken along a line XVI-XVI in FIG. 14.

As shown in FIGS. 13 to 16, the pipe 5 includes a treatment instrument insertion conduit 56 that communicates with the air feeding conduit 6, and may have a configuration in which an opening 56w of the treatment instrument insertion conduit 56 is formed on an end face of the proximal end portion 5t2.

In other words, not only the air feeding conduit 6 and the pressure measurement conduit 7, but also the treatment instrument insertion conduit 56 may be formed integrally in the pipe 5.

The treatment instrument inserted into the treatment instrument insertion conduit 56 from the opening 56w protrudes from the outlet 6e of the air feeding conduit 6.

Figure 17:
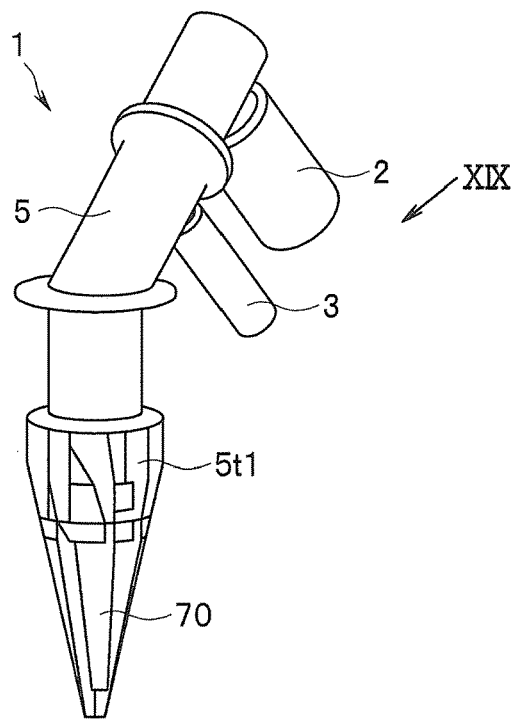
FIG. 17 is a perspective view showing a state where a needle is attached to a distal end portion of the pipe in the pipe for fluid supply shown in FIG. 3.
Figure 18:
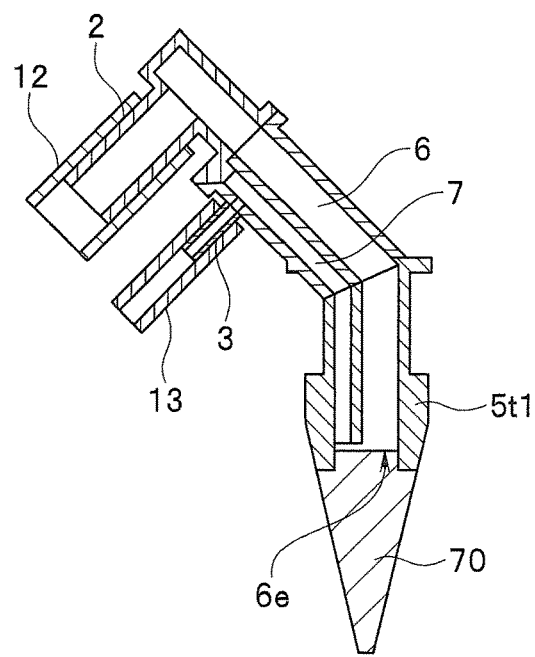
FIG. 18 is a cross-sectional view of the pipe for fluid supply shown in FIG. 17.

Another modification will be described below with reference to FIGS. 17 and 18. FIG. 17 is a perspective view showing a state where a needle is attached to the distal end portion of the pipe in the pipe for fluid supply shown in FIG. 3, and FIG. 18 is a cross-sectional view of the pipe for fluid supply shown in FIG. 17.

When the fixing device 30 is used, the distal end portion 5t1 side of the pipe 5 needs to be inserted until penetrating the gel portion 30j of the fixing device 30. To this end, the distal end portion 5t1 needs to be sharp.

However, since there is a limit to sharpening the distal end portion 5t1 in consideration of an opening diameter of the outlet 6e, a method is known in which the distal end portion 5t1 attached with a needle 70 is inserted as shown in FIG. 17.

Here, since the needle 70 is no longer necessary after the insertion, the needle 70 needs to be removed. When the needle 70 remains attached, the treatment is hindered. In addition, the needle 70 may possibly be detached in the rectum D.

During the removal of the needle 70, an operator uses a method of pulling out the pipe 5 from the rectum D or the gel portion 30j once and then removing the needle 70.

Therefore, as shown in FIG. 18, when the needle 70 is attached to the distal end portion 5t1, the outlet 6e of the air feeding conduit 6 and the outlet 7e of the pressure measurement conduit 7 may be blocked.

According to such a configuration, when the operator forgets to remove the needle 70, since the air cannot be fed into the rectum D due to the blocking of the outlet 6e even when air is fed through the air feeding tube 12 and the air feeding conduit 6, the operator can easily recognize that the needle 70 is not removed.

In such a configuration, in order to prevent the needle 70 from being reattached to the distal end portion 5t1, the needle 70 may not be attached to the distal end portion 5t1 again after being removed.

Figure 19:
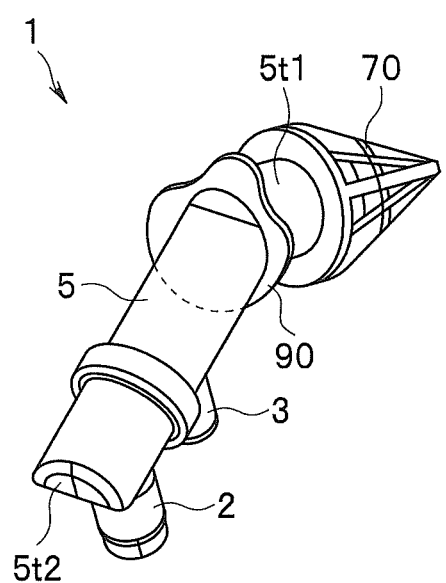
FIG. 19 is a perspective view showing a modification of the pipe for fluid supply shown in FIG. 17 when viewed in a XIX direction in FIG. 17.
Figure 20:
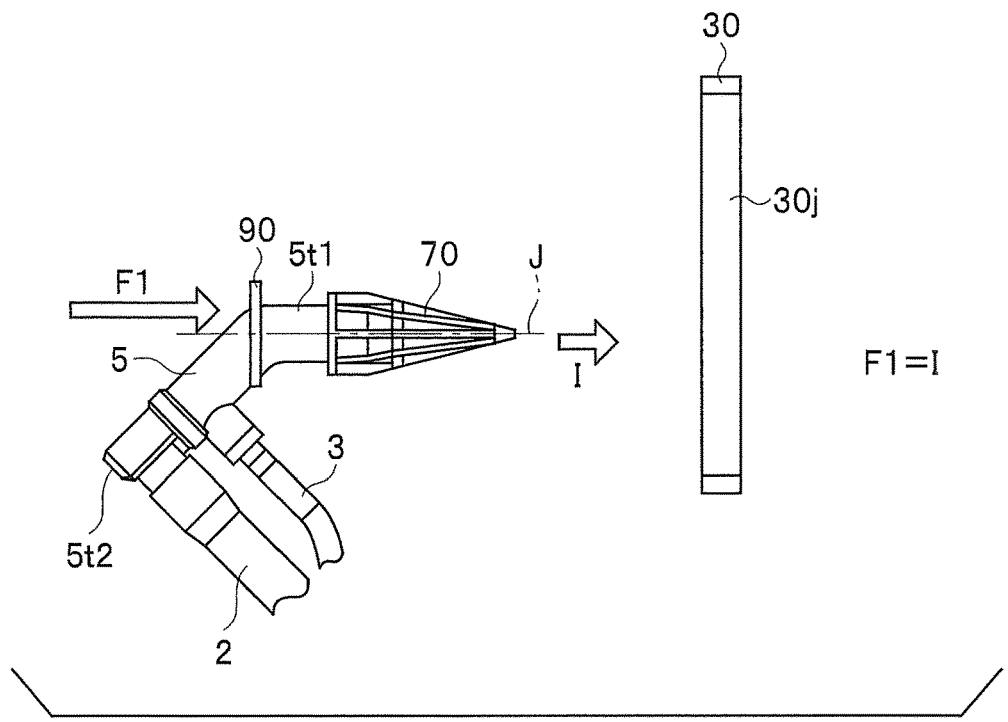
FIG. 20 is a diagram showing a state where a finger rest of the pipe for fluid supply shown in FIG. 19 is pressed and a needle is inserted into a gel portion of a fixing device.
Figure 21:
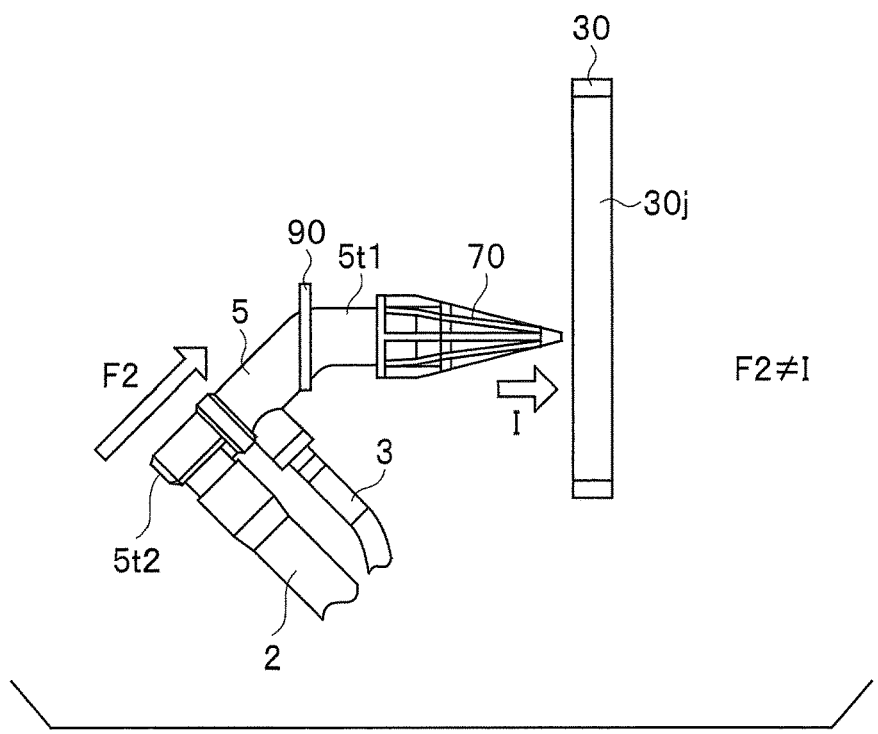
FIG. 21 is a diagram showing a state where the proximal end portion of the pipe in the pipe for fluid supply shown in FIG. 19 is pressed and the needle is inserted into the gel portion of the fixing device.

FIG. 19 is a perspective view showing a modification of the pipe for fluid supply shown in FIG. 17 when viewed in a XIX direction in FIG. 17, FIG. 20 is a diagram showing a state where a finger rest of the pipe for fluid supply shown in FIG. 19 is pressed and the needle is inserted into the gel portion of the fixing device, and FIG. 21 is a diagram showing a state where the proximal end portion of the pipe in the pipe for fluid supply shown in FIG. 19 is pressed and the needle is inserted into the gel portion of the fixing device.

As shown in FIG. 19, a finger rest 90 is provided on an outer periphery of the distal end portion 5t1 side of the pipe 5 in the pipe for fluid supply 1.

The finger rest 90 is used for the operator to efficiently insert (pierce) the needle 70 attached to the distal end portion 5t1 of the pipe 5 into the gel portion 30j of the fixing device 30, and, as shown in FIG. 20, is provided on the outer periphery of the distal end portion 5t1 side of the pipe 5 so as to be substantially perpendicular to an axis J of the needle 70.

Here, when the pipe 5 is not provided with the finger rest 90, the operator is necessary to apply a force F2 to the proximal end portion 5t2 of the pipe 5 when inserting the needle 70 into the gel portion 30j as shown in FIG. 21.

In this case, since the direction in which the force F2 is applied does not coincide with an insertion direction I of the needle 70, the distal end of the needle 70 rotates starting from a contact position with the gel portion 30j, and the force applied to the gel portion 30j from the needle 70 is dispersed, so that the needle 70 hardly pierces through the gel portion 30j.

However, when the finger rest 90 is provided on the distal end portion 5t1 side of the pipe 5, a force F1 applied to the finger rest 90 substantially in parallel with the axis J from the operator is transmitted to the needle 70 coaxial with the force F1 as shown in FIG. 20. For the reason, since the force F1 is applied in the insertion direction I of the needle 70, the needle 70 can efficiently penetrate the gel portion 30j.

Figure 22:
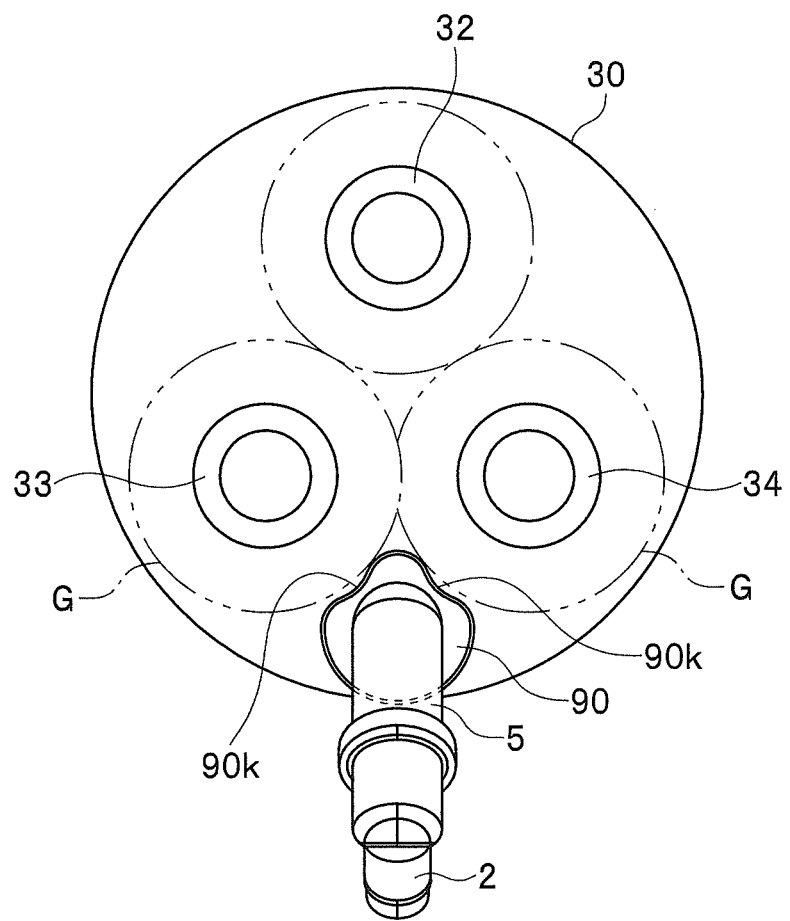
FIG. 22 is a plan view showing a state where the pipe for fluid supply shown in FIG. 2 is stuck in the fixing device when viewed in a IIXII direction in FIG. 2.

FIG. 22 is a plan view showing a state where the pipe for fluid supply shown in FIG. 2 is stuck in the fixing device when viewed in a IIXII direction in FIG. 2.

As described above, the endoscope, the treatment instrument and the like can be inserted into the inlet ports 32 to 34 of the fixing device 30.

As an example, the endoscope can be inserted into the inlet port 32, and the treatment instrument such as forceps can be inserted into the inlet ports 33 and 34.

Here, when the operator performs various treatments by operating the treatment instrument such as forceps inserted into the inlet ports 33 and 34, it is preferable that the treatment instrument be freely moved in the inlet ports 33 and 34 in the inserted state as shown in a movable range G indicated by a two-dot chain line in FIG. 22.

Therefore, two recesses 90k are formed at positions in the finger rest 90 where the treatment instrument interferes, that is, in the movable range G that is a movable range of the treatment instrument. In other words, the finger rest 90 is located outside the movable range G due to the recesses 90k.

In other words, the finger rest 90 has a clover shape in plan view in which two recesses 90k are formed.

The planar shape of the finger rest 90 is not limited to the clover shape, but may be any shape such as a planar shape in which three or more recesses 90k are formed, as long as serving as the finger rest.

Accordingly, the finger rest 90 does not hinder the movement of the treatment instrument such as forceps inserted into the inlet ports 33 and 34.

Figure 23:
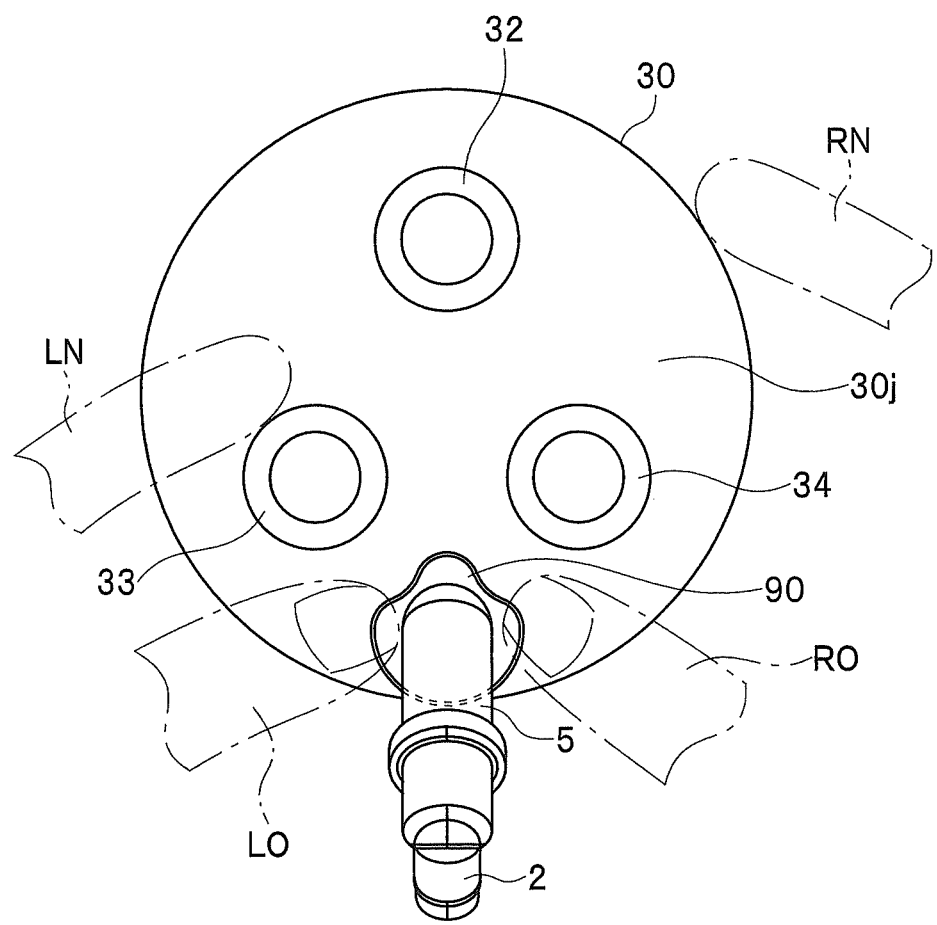
FIG. 23 is a plan view showing a state where the pipe for fluid supply shown in FIG. 22 is inserted into the gel portion of the fixing device with both hands.
Figure 24:
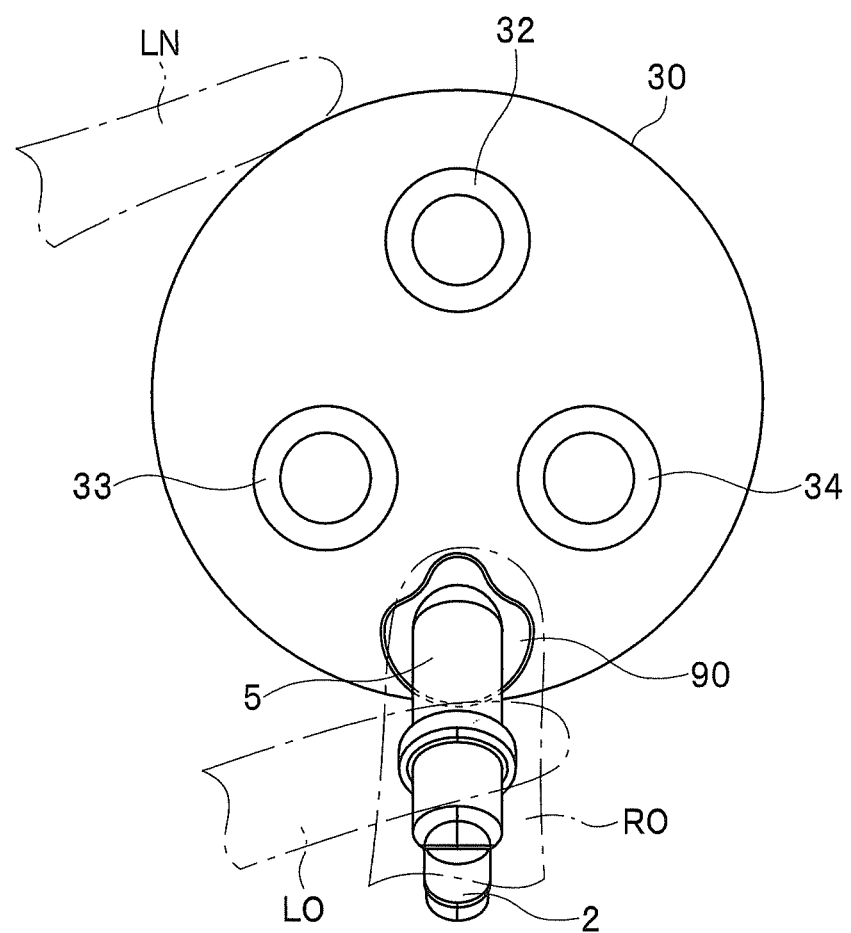
FIG. 24 is a plan view showing a state where the pipe for fluid supply shown in FIG. 22 is inserted into the gel portion of the fixing device with one hand.
Figure 25:
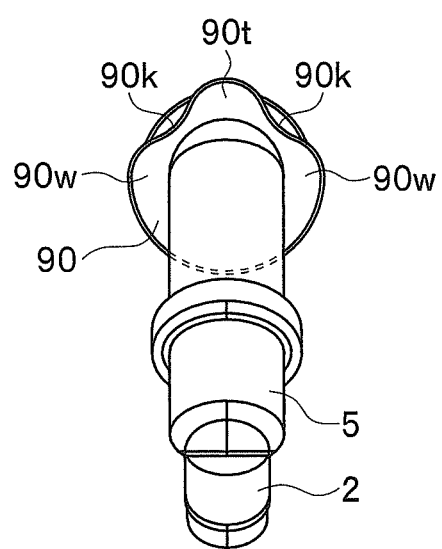
FIG. 25 is an enlarged plan view showing the pipe for fluid supply shown in FIG. 22.

FIG. 23 is a plan view showing a state where the pipe for fluid supply shown in FIG. 22 is inserted into the gel portion of the fixing device with both hands, FIG. 24 is a plan view showing a state where the pipe for fluid supply shown in FIG. 22 is inserted into the gel portion of the fixing device with one hand, and FIG. 25 is an enlarged plan view showing the pipe for fluid supply shown in FIG. 22.

When the operator inserts the needle 70 of the pipe 5 in the pipe for fluid supply 1 into the gel portion 30j, a method of pushing the finger rest 90 described above with a left thumb LO and a right thumb RO in a state where the gel portion 30j is supported by a middle finger LN of the left hand and a middle finger RN of the right hand as shown in FIG. 23, or a method of pushing the finger rest 90 with the right thumb RO in a state where the fixing device 30 is supported by the thumb LO and the middle finger LN of the left hand as shown in FIG. 24 is considered.

At this time, as described above, the finger rest 90 has a clover-like planar shape. Thus, both side portions 90w of a convex portion 90t formed by the recesses 90k may be pushed when the finger rest 90 is pushed with both hands as shown in FIG. 23, and the convex portion 90t may be pushed when the finger rest 90 is pushed with one hand as shown in FIG. 24.

In other words, the finger rest 90 is formed in a shape that can be easily pushed with both hands as shown in FIG. 23 and with one hand as shown in FIG. 24.

The shape of the finger rest 90 shown in FIGS. 19 to 25 described above can also be applied when the pipe for fluid supply 1 is inserted into an insertion target other than the fixing device 30.

In the present embodiment and the modifications described above, the subject is the rectum D as an example, but may be any part of the body of the examinee B without being limited to the rectum, and it goes without saying that the present embodiment and the modifications are applicable not only to medical applications but also to industrial applications. In any case, as described above, the present embodiment is particularly effective when the pressure is measured in real time and the air is supplied to the small space.

Furthermore, the present invention is not limited to the above-described embodiment, but can be appropriately modified within a range of the gist or idea of the invention that can be read from the claims, the entire description, and the drawings.

What is claimed is:

1. A pipe for fluid supply, comprising:
    a pipe body configured to be attached to a body wall of a subject and configured integrally with an air feeding conduit configured to feed air into the subject and a pressure measurement conduit configured to measure a pressure in the subject;
    first and second openings provided respectively at a proximal end of the air feeding conduit provided in the pipe body and at a proximal end of the pressure measurement conduit provided in the pipe body;
    third and fourth openings provided respectively at a distal end of the air feeding conduit provided in the pipe body and at a distal end of the pressure measurement conduit provided in the pipe body;
    a first tube connection portion in fluid communication with the first opening of the air feeding conduit such that a first angle between a direction of the air feeding conduit extending from the third opening and a direction of the first tube connection portion extending from the first opening is 30° to 60°;
    a second tube connection portion in fluid communication with the second opening of the pressure measurement conduit such that a second angle between a direction of the pressure measurement conduit extending from the fourth opening and a direction of the second tube connection portion extending from the second opening is 30° to 60°; and
    a protrusion provided on an outer periphery of the pipe body, the protrusion configured to be pressed distally when a distal portion of the pipe body having the third and fourth openings is inserted into an insertion target, the protrusion extending from the pipe body entirely around the outer periphery of the pipe body.

2. The pipe according to claim 1, wherein the fourth opening provided at the pressure measurement conduit is disposed proximally relative to the third opening provided at the air feeding conduit.

3. The pipe according to claim 1, wherein the protrusion is provided on the outer periphery of the distal portion of the pipe body, the protrusion is configured to be pressed distally when a distal end of the pipe body is inserted into an insertion target.

4. The pipe according to claim 1, wherein a needle configured to be inserted into the insertion target is detachably attached on the distal portion of the pipe body.

5. The pipe according to claim 1, wherein the protrusion includes a plurality of recesses formed on the outer periphery of the distal end portion.

6. The pipe according to claim 1, wherein the first angle and the second angle are each 45°.

7. The pipe according to claim 4, wherein the protrusion is provided substantially perpendicular to an axis of the needle.

8. The pipe according to claim 5, wherein
    the insertion target is a fixing device fixed to the subject, and
    the plurality of recesses are formed in a movable range of a treatment instrument inserted into an inlet of the fixing device, and the protrusion is located outside the movable range.

9. An air feeding system comprising:
    the pipe according to claim 1;
    an air feeding tube having an end connected to the first tube connection portion;
    a pressure measurement tube having an end connected to the second tube connection portion; and
    a fluid supply device connected to an other end of the air feeding tube and an other end of the pressure measurement tube and configured to feed air into the subject through the air feeding tube and the air feeding conduit and to measure the pressure in the subject through the pressure measurement conduit and the pressure measurement tube.

10. A pipe for use with a medical fluid supply system, the pipe comprising:
    a first pipe comprising:
        a distal end portion configured to be attached to a subject, the distal end portion extending along a first axis;
        a proximal end portion extending along a second axis offset from the first axis; and
        a first conduit provided inside the distal end portion and the proximal end portion,
    a second pipe provided at the proximal end portion, the second pipe being in fluid communication with the first conduit, and the second pipe having a third axis offset from the second axis; and
    a protrusion extending from the first pipe entirely around an outer periphery of the pipe body;
    wherein a first angle between the first axis and the third axis is 30° to 60°.

11. The pipe according to claim 10, wherein
    the first pipe comprises a second conduit different from the first conduit, and the pipe further comprises:
    a third pipe provided at the proximal end portion, the third pipe being in fluid communication with the second conduit, and the third pipe having a fourth axis.

12. The pipe according to claim 10, wherein the protrusion is configured to be pressed distally when the distal end portion of the pipe is inserted into the subject.

13. The pipe according to claim 10, wherein the first conduit is an air feeding conduit configured to feed air into the subject.

14. The pipe according to claim 10, wherein the protrusion includes a plurality of recesses formed on the outer periphery of the distal end portion.

15. The pipe according to claim 10, further comprising:
a fixing device configured to be fixed to the subject,
wherein the distal end portion is inserted into the fixing device.

16. The pipe according to claim 11, wherein a second angle between the first axis and the fourth axis is 30° to 60°.

17. The pipe according to claim 11, wherein
the first conduit has a first opening at a distal end side of the first pipe,
the second conduit has a second opening at a distal end side of the second pipe, and
the first opening is provided distally relative to the second opening.

18. The pipe according to claim 11, wherein
the first conduit has a first inner diameter,
the second conduit has a second inner diameter, and
the first inner diameter is larger than the second inner diameter.

19. The pipe according to claim 15, wherein the protrusion is provided outside of the fixing device.

20. A pipe for use with a medical fluid supply system, the pipe, comprising:
a first pipe comprising:
  a distal end portion configured to be attached to a subject, the distal end portion extending along a first axis;
  a proximal end portion extending along a second axis offset from the first axis;
  a first conduit provided inside the distal end portion and the proximal end portion ; and
  a second conduit different from the first conduit;
a second pipe provided at the proximal end portion, the second pipe being in fluid communication with the first conduit, and the second pipe extending along a third axis;
a third pipe provided at the proximal end portion, the third pipe being in fluid communication with the second conduit, the third pipe extending along a third axis; and
a protrusion extending from the first pipe entirely around an outer periphery of the pipe body;
wherein the proximal end portion and the second pipe are configured to move relative to the distal end portion; and
the third pipe is configured to move relative to the distal end portion.

* * * * *